United States Patent
Ackerman et al.

(10) Patent No.: US 7,846,684 B2
(45) Date of Patent: Dec. 7, 2010

(54) ENZYME SYSTEM COMPRISING AN ENZYME BONDED IN A POROUS MATRIX

(75) Inventors: Eric Ackerman, Richland, WA (US); Jun Liu, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 1525 days.

(21) Appl. No.: 09/791,138

(22) Filed: Feb. 21, 2001

(65) Prior Publication Data

US 2004/0106178 A1 Jun. 3, 2004

(51) Int. Cl.
- C12P 1/00 (2006.01)
- C12N 11/14 (2006.01)
- C12N 11/02 (2006.01)
- C12M 1/00 (2006.01)

(52) U.S. Cl. .................. 435/41; 435/176; 435/177; 435/283.1

(58) Field of Classification Search ............... 435/176, 435/177, 180, 182
See application file for complete search history.

(56) References Cited

U.S. PATENT DOCUMENTS

| | | | |
|---|---|---|---|
| 4,539,294 A | 9/1985 | Metcalfe et al. | 435/180 |
| 5,077,210 A | 12/1991 | Eigler et al. | 435/176 |
| 5,645,891 A | 7/1997 | Liu et al. | 427/376.2 |
| 5,705,813 A | 1/1998 | Apffel | |
| 5,843,767 A | 12/1998 | Beattie | 435/287.1 |
| 5,922,299 A | 7/1999 | Bruinsma et al. | 423/335 |
| 5,951,962 A | 9/1999 | Muller et al. | 423/702 |
| 6,326,326 B1 | 12/2001 | Feng et al. | 502/62 |
| 6,635,226 B1 | 10/2003 | Tso et al. | 422/129 |
| 6,696,258 B1 * | 2/2004 | Wei et al. | 435/7.2 |

OTHER PUBLICATIONS

Diaz et al., Journal of Molecular Catalysis B: Enzymatic 2 (1996), pp. 115-126.*
Gimon-Kinsel et al., Studies in Surface Science and Catalysis, vol. 117, 1998, pp. 373-380.*
X Feng et al., "Self-Assembled Monolayers on Messoporous Supports (SAMMS) for RCRA Metal Removal", p. 5.15-5.20. PNNL.
A K Singh et al., "Development of Sensor for Direct Detection of Organopharphates. Part I: Immobilization, Characterization and Stabilization of Acetylcholinesterase and Organophosphate Hydrolase on Silica Supports", p. 1-11. 1999.
PL Havens et al., "Reusable Immobilized Enzyme/Polyurethane Sponge for Removal and Detoxification of Localized Organophosphate Pesticide Spills", p. 2254-2258. 1993.
P Mulchandani et al., "Biosensor for Direct Determination of Organophosphate Nerve Agents. I. Potentiometric Enzyme Electrode", p. 77-85. 1999.
M Huckel et al., "Porous Zirconia: A New Support Material for Enzyme Immobilization", p. 165-179. 1996.
X Feng et al., "Functionalized Monolayers on Ordered Mesoporous Supports", p. 923-926. 1997.

PCT Written Opinion based on PCT/US02/05755, mailed Jun. 14, 2005.
PCT Search Report, mailed Sep. 25, 2003, PCT/US 02/05755.
Kanno et al., "Enhanced Enzymatic Reactions in a Microchannel Reactor," Aust. J. Chem.,55, 687-690, (2002).
Lei et al., "Entrapping Enzyme in a Functionalized Nanoporous Support," J. Am. Chem. Soc., 124, 11242-11243, (2002).
"Applications for Enzymatic Microreactors," web page (1999).
Humphrey et al., "Enzyme immobilisation using SBA-15 mesoporous molecular sieves with functionalized surfaces," J. Molec. Catal. B: Enzymatic 15, 81-92 (2001).
Gavrilidis et al., "Technology and Applications of Microengineered Reactors," Trans IchemE, 80, part A, 3-30 (Jan. 2002).
Takahashi et al., "Immobilized enzymes in ordered mesoporous silica materials and improvement of their stability and catalytic activity in an organic solvent," Microporous and Mesoporous Materials, 44-45, 755-762 (2001).
Washmon-Kriel et al., "Cytochrome c immobilization into mesoporous molecular sieves," J. Molec. Catal. B:Enzymatic 10, 453-469 (2000).
Humphrey et al., "Enzyme Immobilization using siliceous mesoporous molecular sieves," Microporous and Mesoporous Materials, 44-45, 763-768 (2001).
Han et al., "Mesoporous Silicate Sequestration and release of Proteins," J. Am. Chem. Soc. 121, 9897-9898 (1999).
Ackerman et al., "Enzymatic Microreactors," AIChE.
Liu et al., "Molecular Assembly in Ordered Mesoporosity: A New Class of Highly Functional Nanoscale Materials," J. Phys. Chem. A 2000, 104, 8328-8339 (Sep. 2000).
Richins et al., "Expression, Immobilization, and Enzymatic Characterization of Cellulose-Binding Domain-Organophosphorus Hydrolase Fusion Enzymes," Biotechnology and Bioeng., 69, 591-596 (Sep. 2000).
Takahashi et al., "Catalytic Activity in Organic Solvents and Stability of Immobilized Enzymes Depend on the Pore Size and Surface Characteristics of Mesoporous Silica," Chem. Mater. 12, 3301-3305 (Nov. 2000).
Taupin et al., "Surexpression Dans E. coli Et Purification D'une Enzyme Bacterienne Degradant Les Organophosphores La Phosphotriesterase De Flavobacterium SP," Trav. Scient., 177-178 (1997).
Yan et al., "Recent Progress on Immobilization of Enzymes on Molecular Sieves for Reactions in Organic Solvents," Applied Biochem. And Biotech., 113-129 (2002).

* cited by examiner

*Primary Examiner*—David M Naff
(74) *Attorney, Agent, or Firm*—Frank Rosenberg; Derek H. Maughan

(57) ABSTRACT

A protein system is described in which a protein is bound within a matrix material that has pores that are sized to achieve excellent properties such as: activity, protein density, and stability. In a preferred embodiment, the pore sizes range from 50 to 400 Å. One protein that has demonstrated surprisingly good results in this system is OPH. This protein is known to degrade organophosphorus compounds such as are found in chemical weapons and pesticides. Novel methods of forming the protein system and methods of making OPH are also described.

25 Claims, 3 Drawing Sheets

```
CGTCATGACGCCCGCAAGGTCGGTGACAAGAACCGCGCCGGGTTAGTCACAGTGATGCCTGCCAGCGTTTGCTGTGGGAC
GCCCTTCTCTCGTAGGAATGGGATCACTCTCAGTGGAATGAAGGCCATCCCGTCGGGGTTCACGCGATCCATCACGTCCA
TGATGTTGGTGACATAGCTCGAAAACCCGAACAGCCAGTCATTCGAAACGAGGATTTGTTTCATGTAGCCTTGGTCGATG
AGCGCCTTGATCAAGAGAGCCCGTGTTTGCCACGAACGGATGCCCAGGAGGGCTGATGCACTCGCATTATCTTCTAGACC
AATCGCACTGTGCGGGATGTGGTCTAGACCGATGAGGTATCCGCGCGCAGCGAGGGCGGTGAGATAGCTCAAATCGTCAG
TATCATCGCTGTGACCAATACAAACCCGTGAGGGGCTCAAGCCTTCGGACTCAAAAATGGCGGCCTGCTGCTCACCATCG
CGCTGACTTGCTGCCGTGTGAGTGGTTACCGGAACACCGGTGGCCAAGCTGGCCCGGGCGGCCGCCTTTAACACTAACTC
CTGAAAGGGGTCGCCTTGCCTGTGGTCGCGACCTTGATAATGCCCGCCCTAATTCCGGTGTCTTCGATGCCATATTGAA
TCTCACGCAGGAAGAACTGTGTGAGTTCCTCTACACTCCTCAATCGCATCGAAAGTGGCGGGTCGAACCACAAGCCGGTC
GCCGCCACGATATGAACGTCGGCAGCCCGCGAAACCTCGGCCAATAAACTGACGTCGCGACCGATATCGAAAGTCGACAC
ATCGACAATCGTTCGCACGCCAGCCGCTCTGGCGCGGCGCAATCCTCTCACAGCCTTTTCCGCTAGAGCTTTGCGGCTAC
CGAAGAACTCTGGCCAAGCACGCAAGAATCCTGCCGAGCTGCCGCAGATGTGCTCGTGAGTCAGTGTGAAACCCGCTTCA
GAGATTGTGATAGGACCACGAACGGTGTTGATACGGTCACCGGTACCGATAGACATATGTATATCTCCT
```

Fig. 3

```
MSIGTGDRINTVRGPITISEAGFTLTHEHICGSSAGFLRAWPEFFGSRKALAEKAVRGLRRARAAGVRTIVDVSTFDIGR
DVSLLAEVSRAADVHIVAATGLWFDPPLSMRLRSVEELTQFFLREIQYGIEDTGIRAGIIKVATTGKATPFQELVLKAAA
RASLATGVPVTTHTAASQRDGEQQAAIFESEGLSPSRVCIGHSDDTDDLSYLTALAARGYLIGLDHIPHSAIGLEDNASA
SALLGIRSWQTRALLIKALIDQGYMKQILVSNDWLFGFSSYVTNIMDVMDRVNPDGMAFIPLRVIPFLREKGVPQQTLAG
ITVTNPARFLSPTLRAS
```

ENZYME SYSTEM COMPRISING AN ENZYME BONDED IN A POROUS MATRIX

This invention was made with Government support under contract DE-AC0676RLO 1830 awarded by the U.S. Department of Energy. The Government has certain rights in this invention.

FIELD OF THE INVENTION

The present invention relates to proteins in porous supports, methods of supporting proteins, and methods of using supported proteins. The invention also provides an improved method for making organophosphorous hydrolase ("OPH").

BACKGROUND OF THE INVENTION

The usefulness of proteins for facilitating chemical reactions outside biological organisms has long been known and used to great advantage. There is the potential for much greater use of proteins in facilitating a much larger variety of reactions and facilitating these reactions on a larger scale. However, there are many challenges to be overcome before this potential can be fully realized. These challenges include: the need for highly active protein systems; the need for protein systems that maintain high activity under a range of conditions; and the ability to densely pack active protein onto a porous support.

One example of a protein that is useful for catalyzing a variety of useful reactions is organophosphorous hydrolase, ("OPH"). OPH is an enzyme that might be used to inactivate chemical weapons or organophosphorous pesticides. Chemical weapons (i.e. nerve gases, especially sarin and VX) and organophosphorous pesticides (e.g. parathion, paraoxon and acephate) are highly toxic to higher organisms. Therefore, there is a need for methods of cleaning up undesirable discharges of the chemical weapons and organophosphorous pesticides in accidental spills or production plant contamination. The OPH enzyme offers the potential to inactivate chemical weapons or organophosphorous pesticide without the need for complex and expensive incineration facilities. Despite its potential, the lack of suitable methods for the large scale production of systems with active and stable OPH have limited the application of this enzyme.

The present invention provides improved protein systems that can better meet the challenges described above. Although the invention generally applies to immobilized enzyme systems, etc., in some specific examples, the invention also provides an improved method for making OPH and systems containing active OPH.

SUMMARY OF THE INVENTION

One concept of the invention is the engineering of support structures that match protein sizes to support structure pore sizes. It has been surprisingly found that well-matched sizes can produce protein systems having desirable qualities such as high activity, enhanced stability, and a relatively high density of active protein. Coupling of proteins in pores that are either too small or too large results in inferior properties. Other factors, such as surface area, pore density, pore uniformity and distribution, protein population within a support, and type and density of cross-linking sites may also be utilized to control the characteristics of the protein system.

In one aspect, the invention provides a protein system for use in facilitating chemical reactions. The system includes a porous matrix material that has pores within a solid matrix. In another aspect, the protein system comprises: a porous matrix material having a pore volume wherein at least 90% of the pore volume is composed of pores having sizes in the range of 50 to 400 Å, and a chemically-active protein bonded to the matrix material. "Bonded" refers to covalent, ionic and/or electrostatic attachment to the matrix material. In preferred embodiments, the protein is covalently bonded to the matrix through coupling groups.

In another aspect, the protein system comprises: a porous matrix material being sized such that the protein system comprises 8 to 125 mg of protein per gram of matrix material and wherein the protein in the protein system exhibits an activity of at least 65% that of the activity of the protein in the active state.

The invention also provides a method of forming a protein system comprising the steps of: providing a porous matrix material having a pore volume wherein at least 90% of the pore volume is composed of pores having sizes in the range of 50 to 400 Å, and reacting the porous matrix material with a protein so that the protein chemically bonds to the porous matrix material.

The invention also provides a method of making OPH. In this method, a host cell is transfected with a vector comprising a sequence encoding OPH, the sequence being operably linked to a T7 expression control sequence. The transfected host cell is cultured under conditions permitting expression under the control of the expression control sequence. The OPH is purified from the cell or the medium of the cell.

The protein system is engineered to match the size of the individual protein with the size of the individual pores, in preferred embodiments, the volume of the individual protein occupies between 5 and 40% of the average volume of each pore.

The invention also includes methods of using these systems in facilitating chemical processes (i.e., processes of making chemicals) such as hydrolysis, oxidation, hydrogenation, and proteolysis. The invention also encompasses the use of active enzymes in porous supports in filtration equipment for individual soldiers, pesticide workers, vehicles, aircrafts, ships and buildings such as civilian and military defense shelters, to perform detoxifications.

Various embodiments of the present invention can provide numerous advantages including: high protein activities on a porous support; stability under a variety of conditions; high densities of active protein; capability in industrial-scale applications; and providing environmentally safe methods of destroying chemical weapons and organophosphorous pesticides, and avoid the dangers inherent in burning these materials. Other advantages can be envisioned in view of the following descriptions and examples.

BRIEF DESCRIPTIONS OF THE DRAWINGS

FIG. 3 is the relevant DNA sequence from the construct's BamH I to Bgl II site that encompasses the region immediately preceding the T7 promoter to just beyond the OPH stop codon, SEQ ID: 2.

FIG. 4 is the OPH amino acid sequence, SEQ ID: 1.

DETAILED DESCRIPTION OF THE INVENTION

Figure 1:
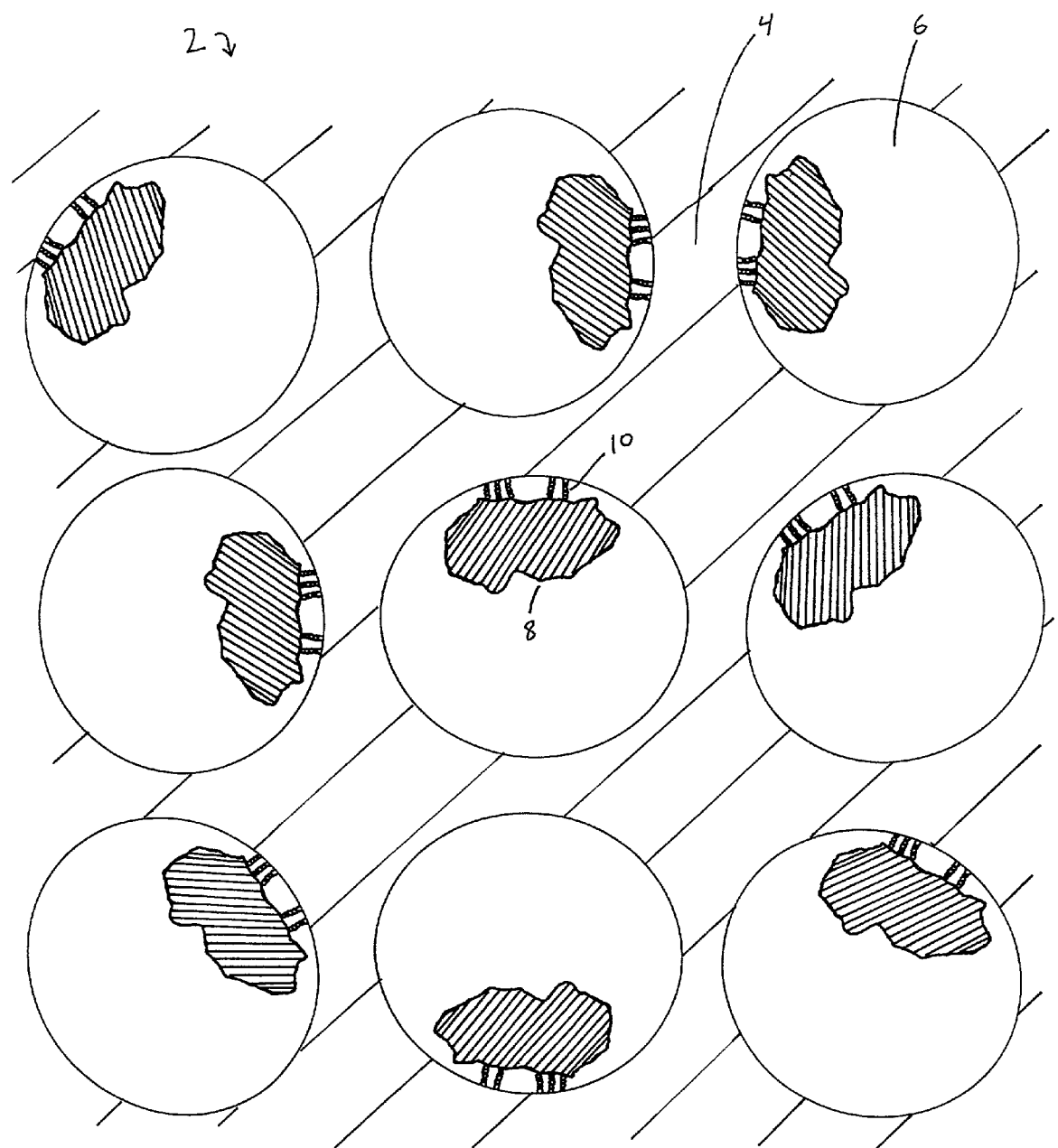
FIG. 1 is a conceptionalized, cross-sectional representation of an enzyme disposed in a porous substrate.

A conceptual illustration of one embodiment of the protein system 2 of the present invention is shown in FIG. 1. A matrix material 4 has pores 6 containing protein 8. The protein 8 is connected to the matrix via connecting moieties 10. Many variations of this structure are possible. For example, while the figure illustrates a single protein in each pore, in many embodiments some pores will contain multiple proteins while other pores contain none. The present invention is not limited to the embodiment illustrated in FIG. 1.

The porous matrix material preferably has a pore volume wherein at least 90% of the pore volume is composed of pores having sizes in the range of 50 to 400 Å, more preferably, 100 to 200, and still more preferably 100 to 120 Å. For purposes of the present invention, pore size distribution is measured by $N_2$ adsorption using techniques that are well-known in the art. For materials with especially large pores, $N_2$ adsorption may need to be supplemented by mercury porisimetry or microscopy to get an accurate pore size distribution. As is conventional, "pore size" refers to pore diameter. In the protein system, the pore size distribution is to be measured without protein in the matrix—for measurement purposes, protein can be removed from the matrix by proteases or other appropriate means. For measurements on protein systems, the coupling agents remain bound to the matrix during measurement of pore size distribution. For purposes of characterizing methods of the present invention, or, of characterizing protein systems according to the method of making them, the pore size distribution of the porous matrix material is measured without coupling agents. The composition of the matrix material can vary, but is preferably an inorganic-oxide-containing material. Inorganic oxide based materials (such as silica-based materials) offer advantages over many organic supports—these advantages can include mechanical strength and chemical and thermal stability.

In preferred embodiments, the protein system comprises a coupling agent disposed between the inorganic porous matrix and the protein. The unreacted (that is, before reacting with a protein) inorganic oxide support typically has surface hydroxyl groups. Preferably, these surface hydroxyls are reacted with relatively low molecular weight organic compounds to form a functionalized monolayer. Treatment with the appropriate coupling agent can produce selected functionalizing moieties on the surface of the porous support. Preferred coupling moieties are mercapto (—SH), amino (—$NH_2$), carboxyl (—COOH), hydroxyl (—OH), and azido (—$N_3$). A particularly preferred embodiment utilizes the functionalized mesoporous support described by Feng et al. in "Functionalized Monolayers on Ordered Mesoporous Supports," Science, vol. 276, 923-926 (1997). As described in the article by Feng et al., the surface hydroxyls can be reacted with mercaptopropyltrimethoxysilane, $(MeO)_3Si(CH_2)_3SH$, to form a functionalized surface with terminal mercapto groups. Functionalized surfaces are superior to the nonfunctionalized surfaces because they provide better and more controllable chemical environments and bonding to proteins.

Where the surface of the porous matrix material is functionalized, it has been found that the degree of functionalization (as measured by surface coverage, where surface coverage is determined by transmission electron microscopy as described in the above-mentioned article by Feng et al.) effects the activity level of the bonded protein. Preferably, surface coverage is between about 20 and 70%, more preferably, between 20 and 50%. Too many coupling moieties can reduce activity while too few reduces covalent attachment of the protein to the matrix and can reduce the stability of the protein system.

Proteins are polymeric organic compounds comprising more than about 100 amino acid residues, and typically having molecular weights in the range of about 8,000 to about 300,000 daltons. Of most interest in the present invention are chemically active proteins, that is, those proteins that are capable of facilitating a chemical process such as hydrolysis, oxidation, reduction, oxygen transport, optical inversion, dehydrogenation, elimination, etc. More preferred are enzymes, that is, those proteins that catalyze chemical reactions. One particularly preferred protein is organophosphorus hydrolase (OPH) which is known and has been reported in the literature, see, for example, Muchandani et al., "Biosensor for direct determination of organophosphate nerve agents. Potentiometric enzyme electrode," Biosensors & Bioelectronics, 14, 77-85 (1999).

A protein can be comprised of amino acids that are all connected through covalent bonds. Proteins can also be comprised of subunits that are held together by non-covalent interactions. For example, hemoglobin is a protein that is comprised of four subunits. Proteins can also include other components such as metal atoms, porphyrin rings, and other manmade or naturally occurring modifications. OPH is a dimeric enzyme that has a diameter of about 45 to 80 Å with a volume of about $1.95 \times 10^5$ Å$^3$. Thus, if a protein system were designed such that OPH occupied 10% of the average pore volume, the matrix would have an average pore volume of about $1.95 \times 10^6$ Å$^3$.

Protein size in the present invention is defined in the conventional sense based on the radius of gyration in the non-denatured state. In the protein systems of the present invention, a preferred type of proteins are enzymes having volumes in the range of $0.5 \times 10^5$ Å$^3$ to $3 \times 10^5$ Å$^3$, because proteins within this size (volume) range are especially advantageous in the porous matrices of the protein systems of the present invention.

The protein in the matrix can be compared to the protein in the "active state." In the present invention, the definition of activity (or "unit activity") for an immobilized protein is the same as the accepted definition for the non-immobilized protein. Activity units are defined in terms of the quantity of protein required to produce a product from a known or characterized substrate in certain buffer conditions at a certain temperature for a specified time. For many enzymes and classes of enzymes, there are commonly accepted activity units. One source of commonly accepted activity units is the Worthington Enzyme Manual (available from the Worthington Biochemical Corporation, Freehold, N.J.). In the present invention, the activity of OPH is defined as described in Dumas et al., J. Biol. Chem., v. 264, p 19659 (1989); an activity unit is the hydrolysis of 1 micromole of paraoxon per minute at 25° C. in 100 mM CHES at pH 9, typically monitored the change in absorbance at 400 nm when the paraoxon substrate is hydrolyzed to diethyl phosphate and p-nitrophenolate anion assuming the extinction coefficient, $\epsilon_{405}$=17,000 $M^{-1}$ cm$^{-1}$. In preferred embodiments, the protein of the invention is at least 50% of the activity in the active state, more preferably at least 75%. We have found that activity of the OPH-containing protein systems have excellent activity. In preferred embodiments, proteins, in systems of the present invention, have activities of 65 to 95%.

While there is an enormous variety of proteins, there is also an enormous overlap in the chemical moieties that make up the protein structure. The same types of amino acids are common to most proteins. This similarity in chemical moieties enables the same coupling techniques to be used to bond proteins onto supports. For example, the sulfhydryl of cysteines, the amino and carboxyl-terminal amino acids, and the amino groups of arginine and lysine, regardless of the protein in which these moieties reside, can typically be similarly reacted with coupling agents or the matrix surface.

In most instances, the protein is not directly bonded to the support. In most cases, a connecting moiety or moieties bonds to the support and the protein. For example, the coupling agent can be reacted via hydroxyl moieties on the support with amines on the protein (see, for example, U.S. Pat. No. 5,077,210 which is incorporated herein by reference). These connecting moieties are preferably organic moieties having a chain length of 2 to 20 atoms, more preferably 4 to 10 atoms. Preferably, each protein is bound to the matrix via at least one coupling moiety, more preferably via 2 to 10 moieties. The number of moieties bound to each protein can be determined by appropriate analytical techniques, for example, by cleaving off the bound proteins and analyzing the cleaved molecules by mass spectrometry. There are a large number of known coupling agents for connecting surface hydroxyls to proteins. For example, a coupling agent can have a siloxane ($-Si(OR)_x$) terminal group that forms oxo bonds to the surface, a flexible organic chain (e.g., $(CH_2)_n$), and a thiol ($-SH$) terminal group that bonds with a protein.

The protein system combining the support and attached protein can be difficult to characterize with chemical precision. However, the system can be characterized by measurable properties. Measurable properties that can define various embodiments of the invention include: pore size, pore volume, pore size distribution, surface area, activity, density of protein in support, density of system, and strength of system. It has been discovered that superior properties can be obtained by engineering supports with pore sizes (or pore volumes) that correspond to protein sizes (or protein volumes). Preferably the volume of a protein is between 5 and 40% of the average pore volume (where, for purposes of this metric, the average pore volume is based only on those pores in the size range of 50 to 400 Å), more preferably the volume of a protein is between 10 and 25% of the average pore volume. This size matching of protein to pore size can produce surprising improvements in activity and stability. Although the mechanisms causing these improved properties are not fully elucidated, it is believed that the confinement of the protein may help to direct reactive species into the protein and may prevent the protein from irreversibly unfolding. Protein volume can be measured by biophysical methods such as analytical ultracentrifugation or x-ray crystallography. Preferably, the activity, measured per protein molecule, is at least 60% of the protein's activity in the active state. Preferably, the system comprises less than 40 volume % protein; more preferably 5 to 40 volume % protein; still more preferably 10 to 25 volume % protein.

Another advantage obtainable by the present invention is high surface area, as measured by $N_2$ adsorption, of the protein system. As with pore size, surface area is measured on the functionalized surface for protein systems and on the unfunctionalized matrix material for the invention defined by methods and systems made by these methods. Surface area is preferably at least 700 $m^2/g$; more preferably at least 900 $m^2/g$. The upper limit of surface area may be limited by the upper limit of the mesoporous matrix materials of the type described by Feng et al. and similar materials. Another advantage of the present invention is that it can produce a relatively dense protein system. Preferably, the protein in the system has a density of at least 8 mg per gram of matrix material; more preferably a density of 8 to 125 mg per gram of matrix material. The inventive systems can be characterized by exhibiting any one of its properties or several of its properties in various combinations. For example, in a preferred embodiment the protein system exhibits an activity of 65 to 95% that of the active protein and has a density of 8 to 125 mg per gram of matrix material.

Proteins can be prepared by known procedures and, in preferred embodiments, do not need special procedures before reaction with coupling agent(s) to bond to the support. Preferably, prior to bonding within the matrix, the protein should be about 95% pure in an aqueous solution that stabilizes activity, and the buffer should not hinder the coupling chemistry.

In the inventive method of preparing OPH, a host cell is transfected with a vector comprising a sequence encoding OPH, the sequence being operably linked to a T7 expression control sequence. The transfected host cell is cultured under conditions permitting expression under the control of the expression control sequence. The OPH is purified from the cell or the medium of the cell. In preferred embodiments, the vector is provided with the sequence encoding OPH operably linked to the T7 expression control sequence. Preferably, the OPH has an activity of about 13,000 units/mg. Preferably, the vector is a plasmid. The host cell can be a prokaryotic cell, eukaryotic cell, or yeast cell. The prokaryotic cell is preferably a bacterium, more preferably the bacterium is *Escherichia coli*. The yeast cell is preferably *Pichia pastoris*.

The matrix is preferably a mesoporous oxide material made from soluble precursors. Examples of preferred syntheses are provided in U.S. Pat. Nos. 5,645,891 and 5,922,299 and 6,326,326, all three of which are incorporated herein as if reproduced in full below, Liu et al., "Molecular Assembly in Ordered Mesoporosity: A New Class of Highly Functional Nanoscale Materials," J. Phys. Chem., 104, 8328-8339 (August 2000), and the Feng et al. article referenced above.

A typical synthesis for a matrix material was reported by Feng et al., Science, 276, p923 (1997). A CTAC/OH solution was prepared by contacting a CTAC solution with a strongly basic ion exchange resin (DOWEX-1, 0.2 g resin per gram of 29% CTAC solution). 13 g of colloidal silica, 51 g of tetramethylammonium silicate and 28 g of mesitylene were added to each 100 g of CTAH/OH solution. The mixture was sealed in a teflon™-lined vessel and heated at 105° C. for 1 week. The product was recovered by suction filtration, dried at ambient temperature, and calcined at 540° C. for 12 hours in air. The surface of the resulting mesoporous material was functionalized by a variety methods. For example, the surface can be functionalized with thiol groups by reaction with tris(methoxy)mercaptopropylsilane. The resulting functionalized matrix is called a "SAMMS." The percent surface coverage was estimated based on (i) the surface area of the support, (ii) the weight change after the functionalized monolayer was attached, and (3) the ideal loading density that could be achieved on flat surfaces. The percent surface coverage can be verified by electron energy-dispersive spectroscopy (EDS).

As known in the art, various approaches can be used to attach a protein for a support. In a preferred embodiment, the support is pretreated with a coupling agent, such as bis[2-(sulfosuccinimidoxycarbonyloxy)ethyl]sulfone (BSOCOES). Excess coupling agent can be washed out. A protein is subsequently reacted with the coupling-agent-treated surface. Alternatively, protein can first be reacted with the coupling agent, and subsequently reacted with the surface of the matrix. Excess protein can be washed out and recovered.

EXAMPLES

We obtained the OPH gene: SEQ ID NO. 3 (FIG. 3) available from the ATCC and sub-cloned it into 2 vectors purchased from Novagen, pET11a and pET15b. Two Novagen vectors were used so that both a native version of OPH and an OPH containing a His-Tag™ could be produced. We produced multiple clones of both types. These Novagen vectors contain strong promoters and they are designed to maximize desired protein yields. Restriction digests confirmed that we correctly sub-cloned the OPH gene and the resulting constructs yielded active OPH protein: SEQ 1D No. 4 (FIG. 4).

Bacterial expression and purification: After the recombinant OPH protein was linked to the nanoporous substrate, purification steps were carried out. The total expression levels achieved were on the order of 4 g/liter for total protein. We purified ~10 mg/liter active protein from the soluble fraction. Thus, most of the OPH is in inclusion bodies; i.e. it is present in an inactive form. The fact that the protein is present in inclusion bodies simplifies purification. OPH purified directly from washed and centrifuged inclusion bodies appears almost as pure as OPH purified by affinity column chromatography as analyzed by SDS polyacrylamide gel electrophoresis. Large scale methods for recovering activity from inclusion body proteins may be developed through routine experimentation. This simplified purification procedure is suitable for industrial production.

Materials and Methods

Materials:
Diethyl p-nitrophenyl phosphate (paraoxon, 90%), different metals salts, glycerol and all buffers and other salts were purchased from Sigma®-Aldrich®.
Components of fermentor media (Peptone and Yeast extract) were obtained from Gibco BRL, expression vectors (pET11a™, pET15b™) were purchased from Novagen Inc., Madison, Wis. Primers for PCR were ordered from Genosys Inc.
Bulk chromatography media for the protein purification was obtained from Perseptive Biosystems (HS™ and HQ™).
Polypropyl A™ columns as well as nonderivatized silica resin for comparison of OPH linking obtained from Poly LC Inc., Columbia, Md.
Cross-linking reagents for enzyme immobilization were purchased from Pierce Chemical Company, Rockford, Ill.

The Abbreviations Used:
CTAC, cetyltrimethylammonium chloride
OPH, organophosphorous hydrolase,
HEPES, N-2-hydroxyethylpiperazine-N'-2-ethanesulfonic acid,
CHES, 2-(cyclohexylamino)ethanesulfonic acid,
IPTG, isopropylthiogalactoside,
SAMMS, self-assembled monolayers on mesoporous silica,
Sulfo-BSOCOES, bis[2-(sulfosuccinimidoxycarbonyloxy)ethyl]sulfone,
DTSSP, dithiobis(sulfosuccinimidylpropionate).
β-ME, β-mercaptoethanol Matrix Synthesis:
A typical procedure for preparing the mesoporous oxide material used in the Examples is as follows. Mesoporous silica with 300 Å pore diameter was prepared by a liquid crystal templating procedure. Triblock copolymer, Pluronic P123™ (a propylene oxide/ethylene oxide copolymer available from BASF, $M_{av}$=5,600) was used as a structure-directing agent and mesitylene as a pore expending agent. 20 g of Pluronic P123 was dissolved in 150 g of deionized (DI) water and 600 g of 2 M HCl solution at 40° C. with stirring. 31.9 g of mesitylene was then added and kept stirring at the same temperature. 42.5 g of TEOS was added dropwise into the cloudy micelle solution and cured at that temperature for 20 h with stirring. The mixture was aged in a teflon-lined autoclave at 100° C. overnight without stirring. The white solid was filtered, washed with DI water, and air-dried. This solid was calcined at 550° C. for 6h with slow increasing temperature (1° C./min).

In a typical preparation of 20% propylcarboxylic acid functionalized mesoporous silica, 2.0 g of mesoporous silica (average pore size=30 nm, surface area=533 $m^2$/g) was first suspended in toluene (60 mL) and pretreated with approximately a bilayers' worth of DI water (0.64 ml). This suspension was stirred for 2 hours to distribute the water throughout the mesoporous matrix. The hydrated mixture was then treated with 20% (0.288 g) of 1 monolayer's 3-cyanopropyltrimethoxysilane (CPTS) and heated to reflux for 6 hours. The treated mesoporous silica was washed with toluene to remove any unreacted silanes. The air-dried CPTS-SAMMS materials were then treated with 50% $H_2SO_4$ solution and refluxed for 3 hours. After washed with DI water extensively, the white sample was dried under vacuum at 70° C. overnight.

In case of 20% aminopropyl (APTS) and mercaptopropyl (MPTS) functionalized silica, the same procedure was applied without hydrolysis step. To the suspension of 2.0 g of mesoporous silica, toluene (60 mL) and 0.64 g of water and 0.188 g of APTS or 0.206 g of MPTS were added separately. The mixtures were heated to reflux for 6h, and then filtered off, washed with ethanol, and dried under vacuum at 70° C. overnight.

Figure 2:
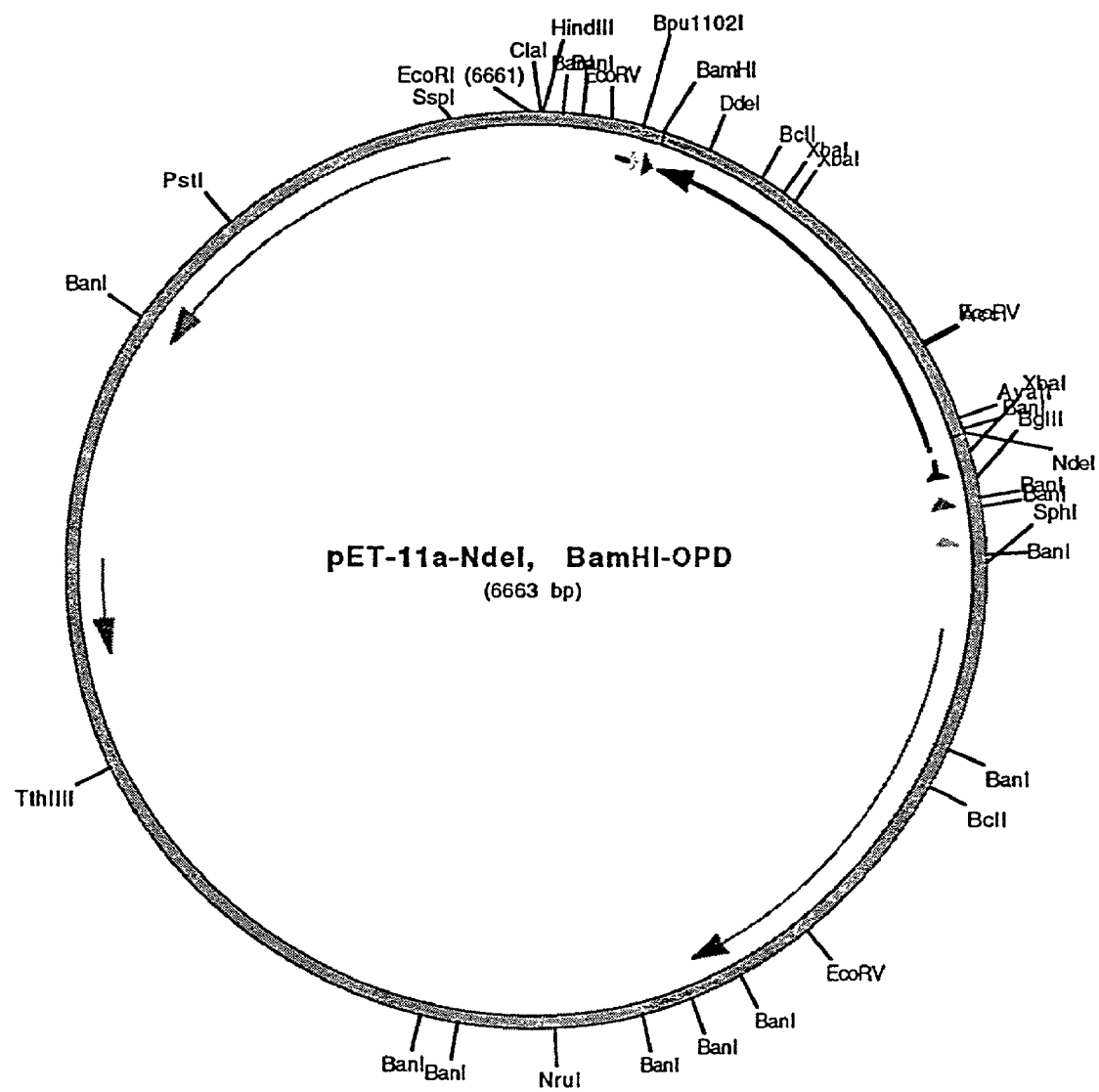
FIG. 2 is a ribbon diagram for OPH plasmid.

OPH Subcloning:
OPH sequence was cloned by PCR using pCMS75 plasmid in *E. coli* FM5 (Amgen Inc.), which had been obtained from American Type Culture Collection, Rockville, Md. (ATCC® #67778).
Primers were designed to yield a PCR (polymerase chain reaction) product from the ATTC clone that would contain the full-length OPH open reading frame as well as appropriate restriction sites at the 5'- and 3'-ends for ligation into the pET expression vectors. For each primer, approximately 15-20 nucleotides were desired for complementarity, while the remainder of the sequence was intended for construction of the essential restriction sites for insertion into the pET vectors. Potential primers were screened with PCR primer software (Primer Prernier™ software, version 4.04, from Premier Biosoft International) to minimize hairpins and optimize potential PCR product, and the indicated sequences synthesized by Genosys (The Woodlands, TX). The primers used were listed as following:
OPH upstream primer, 26-mer: SEQ ID No. 15' TAAATTATCTCTGGCGGTGTTGACAT 3' OPH downstream primer with BamHI restriction site (recognition sequence in bold), 20-mer: SEQ ID No. 2 5' GAAGGATCCAGATGGCGTCA 3'.
OPH sequence: SEQ ID No.3 (FIG. 3) was subcloned using NdeI, BamHI restriction sites into pET11a. The resulting OPH sequence encoded the mature portion of OPH enzyme, i.e., without N-terminal 29 amino acid signal sequence, so that the length of the sequence is 1010 bp, which corresponds to 337 amino acids in total (FIG. 4) or 36,419 Da in MW.
The confirmation of the correct product of cloning was made by PCR and restriction enzyme digest.
A plasmid diagram for OPH is illustrated in FIG. 2.

Expression and Purification:
The organophosphorous hydrolase was purified from *E. coli* expression system using oph-pET11a plasmid and BL21 (DE3) pLyss™, Novagen Inc., as a host strain. (N-terminal His-Tag™ OPH subcloned into pET-15b plasmid) Induction with IPTG was shown to produce a protein which has apparent mobility on SDS gel corresponding to prediction based on the gene sequence of mature native OPH protein without N-terminal signal sequence (about 36 kDa or with the N-terminal His-Tag about 38 kDa). Identity of the recombinant product was also confirmed by aminoacid analysis and appearance of Paraoxon hydrolysis activity in crude cells lysate after induction with IPTG. The general protocol used for propagation of cells in Bio-Flo 3'000 fermenter™ (New Brunswick, Inc.) was as follows:

The *E. coli* cells were grown for 12 hours at 30° C. in a flask, 100 µl of glycerol stock/1L of LB media, 100 µg/ml ampicillin, 35 µg/ml chloramphenicol, and this starting culture was used as inoculums for the fermenter. 500 ml ON culture with OD=0.5 were spun down, washed with fresh LB media, spun again, redissolved in 250 ml of LB without antibiotics, added to the fermenter media, total volume=2.5 L. (NOTE: make sure not to add 1 mM $CoCl_2$ to LB media for ON starting culture, since it kills the cells).

Cells in the fermenter reached mid-log phase after 4 hrs at 37° C. in a medium containing 5 g/l Yeast Extract, 10 g/l Peptone, 5 g/l NaCl, 1 ml/l antifoam, 60 mM $K_2HPO_4$, 15 mM $KH_2PO_4$, 1 mM $CoCl_2$, 1.32 µg/ml thiamine, 100 µg/ml ampicillin, 35 µg/ml chloramphenicol, 10 g/l glycerol and trace metals (10 µM $NH_4Mo_7O_{24}$, $CuSO_4$, $H_3BO_3$, $MnCl_2$, $ZnCl_2$), 50 µM $FeCl_3$, 0.5 mM $CaCl_2$, 1 mM $MgSO_4$. Oxygen level was maintained at 35% using DO-agitation-oxygen triple cascade, setting up agitation range 200 rpm minimum to 800 rpm maximum. Initial glucose concentration in the media was 10 g/l, glucose level was monitored during the run using regular glucose strips and kept to be not less than 2 g/l.

When agitation reached 467 rpm, OD550=5, glucose level was 2 g/l. Thirty-one (31) ml of 40% glucose were added to bring the glucose level to 5 g/l. When agitation reached 700 rpm, OD550=15, glucose level dropped again to 2 g/l. The temperature was lowered to 28° C., the mixture was induced with 0.25 mM IPTG and another 31 ml of 40% glucose were added.

After 4 hrs of induction at 28° C., another 0.25 mM IPTG were added (total of 0.5 mM). The glucose level was 2 g/l again and 63 ml of 40% glucose were added to bring the glucose level to 10 g/l. After 2 more hours of induction, cells obviously continued to grow, temperature was lowered to 24° C. and the cells were left in a fermenter ON for another 14 hrs. Finally, the cells were harvested by centrifugation at 6,000 rpm for 20 min at 4° C.

From 2.5 l of cell culture, about 150 g of wet weight cell paste was isolated and the cell paste was stored at −80 ° C.

We were able to purify from 60 g of cells (corresponds to 1 L of culture) about 90 mg of OPH with activity of 13,294.12 units/mg. This yield can be compared to the literature. Omburo G. A., Kuo J. M., Mullins L. S., and Raushel F. M., in Characterization of the Zinc Binding site of Bacterial Phosphotriesterase. JBC, 1992, v.267(5): 13278-13283 reported getting from 160 g of cells about 298 mg of cobalt phosphotriesterase with activity 8'020 units/mg.

Lai K., Dave K. I., and Wild J. R. (Bimetallic Binding Motifs in Organophosphorous Hydrolase Are Important for Catalysis and Structural Organization. JBC, 1994, 269(24): 16579-16584), which is more difficult to compare, reported purifying 5 mg of OPH per 1 L of culture (probably grown in flasks). They favored using weak promoters for expression (native Plac) versus strong promoters, like T7, because the yield of OPH activity they got with strong promoter constructs was lower (data not shown). All purification steps were performed at 4° C. using pre-cooled equipment and Revco Chromatography Refrigeration cabinets.

The bacterial cells (60 g) were suspended in 420 ml of lysis buffer A, containing 100 mM HEPES pH 8.5, 50 uM $CoCl_2$, 1 mM DTT, antiprotease cocktail (pepstatin, leupeptin and aprotinin), and cells were lysed using French pressure cell 2 times. Soluble protein supernatant obtained by 100,000×g centrifugation for 1 hr (Avanti™, Bechman), was loaded on 500 ml HQ™ anion-exchange column (Perseptive Biosystems) equilibrated in buffer A, with substitution of 1 mM DTT for 5 MM beta-mercaptoethanol (2-me). The column flow rate was 25 m/min.

Flow-through containing OPH was collected, pH was adjusted to 7.5 using 1 M MES, pH 5.5, and applied on a 250 ml HS cation exchange column (Perspective Biosystems), equilibrated in 0.1 M HEPES, pH 7.5, 50 uM $CoCl_2$, 5 mM 2-me. The column flow rate was 25 ml/min.

Flow-through of HS column was retained, enough dry $(NH_4)SO_4$ was added to make final conductivity of the sample to be equal to conductivity of 1 M $H_4)SO_4$ solution (i.e., 105 mS/ml), using a conductivity meter Orion 126, Cell 012210. A sample was loaded on a 180 ml Polypropyl A™ (PolyLC, Inc.) column, equilibrated in 1 M $(NH_4)SO_4$, 0.1 M HEPES pH 7.5, 5 mM 2-me. The column flow rate was 10 ml/min.

After 3 column volume wash with equilibration buffer 10 column volume gradient to 0.1 M HEPES pH 7.5 was applied, OPH was eluted in the very end of the gradient. We were able to purify close to 100 mg of pure OPH from 60 g of cells (corresponds to 1 L of culture).

After concentrating the protein up to 3 mg/ml using Milipore UltraFree® Biomax centrifugal concentrators with 30 K NMWL (30 kDa cut-off) membrane and dialysis against 20% glycerol to 0.1 M HEPES pH 7.5 50 uM $CoCl_2$ protein was aliquoted and stored at −80 ° C. Specific activity was determined as 13,294.12 units/mg (see Table I and summary SDS gel).

The difference in activity of the protein which came as a peak from HIC and the same protein after concentration and dialysis probably may be explained by the buffer exchange. In one case, the buffer contained beta-mercaptoethanol, the competitive inhibitor of OPH activity, and no $CoCl_2$, the other the buffer contained 50 µM $CoCl_2$ and no 2-me.

TABLE I

Purification of OPH (Co in active center)

| Purification stage | Total protein, mgs | Volume, ml | Total activity, units | Purification, fold | Specific activity units |
|---|---|---|---|---|---|
| Cell lysate 100k supernatant 62 g cells | 20,925 | 620 | 1,133,364 (100%) | 1.0 | 54.16 |
| HQ 500 ml flow-through (HS | 10,044 | 1000 | 923,435 (81.48% | 1.69 | 91.94 |

TABLE I-continued

Purification of OPH (Co in active center)

| Purification stage | Total protein, mgs | Volume, ml | Total activity, units | Purification, fold | Specific activity units |
|---|---|---|---|---|---|
| starting material) | | | recovery) | | |
| HS 250 ml flow-through (HIC starting material) | 7,714 | 1240 | 903,529 (79.72% recovery) | 2.16 | 117.13 |
| HIC 180 ml OPH peak | 100 | 180 | 468,465 (41.33% recovery) | 86.5 | 4,684.66 |
| Pure OPH after concentration and dialysis, 3 mg/ml | 90 | 28 | 1,196,473 | not applicable | 13,294.1 |

OPH Immobilization:

Media Used:
1. SAMMS: derivatized with SH—, COO—, NH$_2$— active groups, 5% and 20% coating (5% and % of all available silane groups get modified or derivatized with active groups). Characteristics of the media: 250 Å 12-15 um beads, surface area around 450 m$^2$/g
2. Poly LC Silica: Purchased uncoated, derivatized in PNNL with NH$_2$—, COO— groups, 20% and 100% coating. Characteristics of the media: 300 Å 12 um beads, surface area around 100 m$^2$/g.

After screening for the best linking chemistry that would give the highest density of bound enzyme as well as lowest losses of activity and lowest diffusion limits, we chose linking of OPH through its NH$_2$— groups to NH$_2$—derivatized media.

Many cross-linking agents were tested, among them 2 were found to be especially efficient: Sulfo-BSOCOES, bis[2-(sulfosuccinimidoxycarbonyloxy)ethyl]sulfone, and DTSSP, dithiobis(sulfosuccinimidylpropionate). The advantages of these 2 cross-linking agents are as follows:
  i. Both cross-linking agents have spacer arms (12 Å in length for DTSSP and 13 Å for BSOCOES). A spacer arm is beneficial to avoid steric hindrance.
  ii. Both of them are water soluble due to the sulfo-functioning group.
  iii. Pierce (Rockford, Ill.) recommended PBS as the linking buffer, pH 7.5. This pH is favorable for OPH because OPH tends to aggregate and lose the metal from active center at an acidic pH, i.e., pH lower than 6.5. A higher pH has another advantage: The hydrolysis of NHS-esters proceeds faster at a higher pH. Therefore when we used a higher pH, we obtained a higher molar ratio of cross-linking agent per protein.
  iv. Both produce stable covalent amide bond, which in case of DTSSP is cleavable with thiols (DTT, mercaptoethanol, etc.). This feature could be useful for certain applications.

Standard Protocol for Sulfo-BSOCOES or DTSSP Coupling of OPH to NH$_2$-Derivatized Surface: (Pierce Protocol with Little Modifications)
1. Sulfo-BSOCOES or DTSSP cross-linking reagents (come in tubes) should be stored at −20° C., preferably desiccated, under nitrogen. In practice it is a good idea to use nitrogen glove box or nitrogen bags (filled with nitrogen using a nitrogen tank in a cold room) when work with the cross-linking reagents (i.e. to aliquot the content of the original tube). Always let the reagents come to room temperature before opening the tube.
2. The media that is planned to link OPH to should be well swollen in water. In general we used 500 mg of media/5 ml H$_2$O and made a ~50% slurry (v/v) for SAMMS. This slurry was very stable when stored at +4° C. NOTE: For PolyLC media: 2×more media in dry weight compared to SAMMS should be used (i.e. ~1 g of PolyLC media/5 ml H$_2$O and make a ~50% slurry (v/v)).
3. OPH, 09/02 purification, [3 mg/ml], aliquoted in 2 mls, stored at −80° C., was thawed, and the buffer was changed from 25 mM HEPES pH 8.5, 20% glycerol, 50 uM CoCl$_2$ to 0.1 M carb/bicarbonate, pH 9.0. The NAP-25 column that we used had a max volume of 10 ml. With that, we were able to apply about 2.5-3.0 ml of the max sample volume.
4. Concentrate up to 20 mg/ml using the new Millipore Biomax Ultrafree 4.0 ml 30K CO membrane unit, for 10' at +4° C. Sorvall CF, bucker rotor, at max speed.
5. With a cut yellow tip, added 50% slurry powder in H$_2$O to OPH, in 0.1 M carb/bicarbonate buffer pH 9.0, 90.1 ml volume for 2 mgs. The approximate ratio for the slurry powder is 150 ul 50% slurry/2 mg of protein: 2 types of derivatization (NH$_2$— 20% and 100% coverage) of PolyLC silica, and NH$_2$-SAMMS 20% coverage.
6. Dissolve 1.5 mg or 3 mg or 6 mg Sulfo-BSOCOES or DTSSP in 590 ul of 5 mM MES pH 5. (to get 10×, 25×, and 50×molar ratio of cross-linking agent/protein)
7. Immediately add the cross-linking agent solution (125 ul/2 mg of protein) to each eppendorf tube drop-wise, mixed, put the tube on rotating device, at room temperature for 45 min.
8. Add stop-solution: 1 ml of 1 M Tris pH 8.1, 1 hr at room temperature.
9. Wash with PBS 2 times, 0.5 M NaCl-PBS one time, and PBS one time. Re-suspend in 100 mM HEPES pH 8.5-50 uM CoCl$_2$ and stored at +4° C.
10. Estimate the amount of protein lined to the resin using BCA Pierce kit, allow to react at 37° C. for 30 min.

Example 1

Coupling of OPH to SAMMS-NH$_2$ derivatized surface using Sulfo-BSOCOES 20% coating, with 50×molar excess of cross-linking agent per protein. The standard protocol was followed, thus:
1. A nitrogen glove box filled with nitrogen was used for taking aliquots of the content out of the tubes containing Sulfo-BSOCOES.
2. Five hundred (500) mg of media were used in 5 ml H$_2$O and made a ~50% slurry (v/v). This slurry was very stable when stored at +4° C.

3. OPH, 09/02 purification, [3 mg/ml], aliquoted in 2 ml, stored at −80° C., was thawed, and the buffer was changed from 25 mM HEPES pH 8.5, 20% glycerol, 50 uM $CoCl_2$ to 0.1 M carb/bicarbonate, pH 9.0 using Pharmacia Sephadex G-25 column. The NAP-25 column that we used had a max volume of 10 ml. With that, we were able to apply about 2.5-3.0 ml of the max sample volume.
4. Concentrate up to 20 mg/ml using the new Millipore Biomax Ultrafree 4.0 ml 30K CO membrane unit, for 10 min at +4° C. Sorvall CF, bucker rotor, at max speed.
5. With a cut yellow tip, added 50% slurry powder in $H_2O$ to OPH, in 0.1 M carb/bicarbonate buffer pH 9.0, 90.1 ml volume for 2 mgs. The approximate ratio for the slurry powder is 150 ul 50% slurry/2 mg of protein: 2 types of derivatization ($NH_2$— 20% and 100% coverage) of PolyLC silica, and $NH_2$-SAMMS 20% coverage.
6. Dissolve 6 mg of Sulfo-BSOCOES in 590 ul of 5 mM MES pH 5.
7. Immediately add the Sulfo-BSOCOES solution (125 ul/2 mg of protein) to the eppendorf tube drop-wise, mixed, put the tube on rotating device, at room temperature for 45 min.
8. Add 1 ml of 1 M Tris pH 8.1, 1 hr at room temperature.
9. Wash with PBS 2 times, 0.5 M NaCl-PBS one time, and PBS one time. Re-suspend in 100 mM HEPES pH 8.5-50 uM $CoCl_2$ and stored at +4° C.
10. Use a BCA Pierce kit, allow to react at 37° C., the estimated amount of OPH linked to the resin=25.0 mg/ml media and 125.0 mg/g media.

Example 2

Coupling of OPH to SAMMS-$NH_2$ derivatized surface using Sulfo-BSOCOES 20% coating, with 25×molar excess of cross-linking agent per protein. The procedures were similar to Example 1, except for step 6: 3 mg of Sulfo-BSOCOES were used instead. The estimated amount of OPH linked to the resin=16.0 mg/ml media and 8.0 mg/g media.

Example 3

Coupling of OPH to SAMMS-$NH_2$ derivatized surface using Sulfo-BSOCOES 20% coating, with 10×molar excess of cross-linking agent per protein. The procedures were similar to Example 1, except for step 6: 1.5 mg of Sulfo-BSOCOES were used instead. The estimated amount of OPH linked to the resin=5.0 mg/ml media and 25.0 mg/g media.

Example 4

Coupling of OPH to SAMMS-$NH_2$ derivatized surface using DTSSP 20% coating, with 50×molar excess of cross-linking agent per protein. The procedures were similar to Example 1, except for step 6: 6 mg of DTSSP were used instead. The estimated amount of OPH linked to the resin=25.0 mg/ml media and 125.0 mg/g media.

Example 5

Coupling of OPH to SAMMS-$NH_2$ derivatized surface using DTSSP 20% coating, with 25×molar excess of cross-linking agent per protein. The procedures were similar to Example 1, except for step 6: 3 mg of DTSSP were used instead. The estimated amount of OPH linked to the resin=16.0 mg/ml media and 80.0 mg/g media.

Example 6

Coupling of OPH to SAMMS-$NH_2$ derivatized surface using DTSSP 20% coating, with 10×molar excess of cross-linking agent per protein. The procedures were similar to Example 1, except for step 6: 1.5 mg of DTSSP were used instead. The estimated amount of OPH linked to the resin=5.0 mg/ml media and 25.0 mg/g media.

Example 7

OPH was coupled to PolyLC at 20% and 100% coating surface using Sulfo-BSOCOES and DTSSP, with 10×, 25×, and 50×molar excess of cross-linking agent per protein. The procedures were similar to Example 1 to 6, except for step 2: 1000 mg of PolyLC were used per 5 ml $H_2O$ and made ~50% slurries (v/v).

The estimated amount of OPH linked to the resin is listed in Table II.

TABLE II

| Media | SAMMS-$NH_2$, 20% coating | | | PolyLC, 20% coating | | | PolyLC, 100% coating | | |
|---|---|---|---|---|---|---|---|---|---|
| molar excess x-linking agent | 10 x | 25 x | 50 x | 10 x | 25 x | 50 x | 10 x | 25 x | 50 x |
| OPH bound, mg/ml media | 5.0 | 16.0 | 25.0 | 5.0 | 5.0 | 6.74 | 7.0 | 8.5 | 9.0 |
| OPH bound, mg/g media | 25.0 | 80.0 | 125.0 | 12.5 | 12.5 | 16.85 | 17.5 | 21.5 | 22.5 |

It can be seen that inventive compositions are capable of higher density loading than with conventional silica (PolyLC). Thus, preferred embodiments of the invention can be characterized by loading densities. Preferably the protein system has density that is 2 to about 7 times higher (in mg/g) than PolyLC with the same coating %, more preferably about 5 to about 7 times higher. In a preferred embodiment, the densities are measured at a 20% coating.

Example 8

Effect of Denaturing

Stability to denaturing conditions of OPH-SAMMS and soluble OPH was conducted using urea as the denaturing agent at concentrations of 4 M, 6 M and 8 M. The phrases "Soluble OPH" or "OPH soluble" in the Examples section refers to the non-inclusion body OPH that was released during cell breakage with the French Press and soluble in the buffers indicated for each purification step. The results are shown in Table 3 below.

TABLE III

|  | 4M | | 6M | | 8M | |
| --- | --- | --- | --- | --- | --- | --- |
|  | soluble | imoblized | soluble | imoblized | soluble | imoblized |
| OPH Soluble/ immobilized Activity % | 94 ± 8 | 108 ± 10 | 39.5 ± 0.3 | 72.1 ± 0.7 | 4.0 ± 0.5 | 21.6 ± 0.2 |

The immobilized enzyme was far more stable than the free protein. Thus, preferred embodiments of the invention can be characterized by their stability to denaturing agents. Preferably the protein system has a stability, in 8M urea, that is at least twice as stable as the free protein, more preferably about 3 to about 5 times more stable.

Example 9

Recovery From Dehydration

Dehydration and recovery experiments were conducted using the immobilized OPH-SAMMS and soluble OPH. While soluble OPH retained only 7±1% of its activity, the OPH-SAMMS completely retained its activity (106±8%).

Example 10

Kinetic Properties

A kinetic study was performed with immobilized OPH on SAMMS, immobilized OPH on PolyLC, and soluble OPH. Enzymatic activity was measured using 1 mM paraoxon solution at 25 C and monitoring the change in absorbance at 405 nm when substrate was hydrolyzed to diethyl phosphate and p-nitrophenolate (extinction coefficient 17,000 $M^{-1}$ $cm^{-1}$) in 100 MM CHES buffer, pH 8.0, 50 uM $CoCl_2$. Analysis was with a Hewlett-Packard model 8453 UV/Vis spectrophotometer in kinetics mode equipped with the Thermostable Cell Holder and Cell Stirring Module. Fresh dilutions of substrate were prepared no more than 30 minutes before measurements. SigmaPlot was used to draw linear regressions of the data. The PolyLC (Columbia, Md.) silica was purchased uncoated, and derivitized with amino groups. The pore size of the 12 um beads was 300 Å. Both OPH immobilized of SAMMS and PolyLC have the same $K_m$ as soluble OPH, but demonstrated lower $V_{max}$: 2.83 fold lower for OPH-SAMMS, and 6.44 fold for OPH-PolyLC. That is: OPH-SAMMS has approximately 2.3 times faster reaction rate than OPH-PolyLC. Mass in the table refers to mass of OPH.

|  | OPH soluble | | OPH-SAMMS | | OPH-PolyLC | |
| --- | --- | --- | --- | --- | --- | --- |
| Concentration, μg/ml | 0.150 | 0.375 | 0.16 | 0.40 | 0.15 | 0.40 |
| $K_m$, mM | 0.099 | 0.125 | 0.086 | 0.127 | 0.087 | 0.130 |
| $V_{max}$, AU/s | 0.50 | 1.87 | 0.15 | 0.66 | 0.08 | 0.29 |

Example 11

Stability in Alkaline pH

In this experiment, OPH-SAMMS and soluble OPH were tested for stability under alkaline conditions. After one hour of alkaline pH treatment (1M Tris, pH 12.0), the OPH-SAMMS was found to retain 11.6% of its activity as compared with 0.77% for the soluble OPH, and after 24 hours of this alkaline treatment, the OPH-SAMMS was found to retain 9.9% of its activity as compared with 0.03% for the soluble OPH. The conditions in this example define what is meant by "alkaline conditions" as that term is used in this application. While the example illustrates an OPH system, it should be recognized that the stability advantages provided by the mesoporous matrices of the present invention are general, and it is expected that other proteins will obtain similar stability advantages.

Example 12

Thermal Stability

Experiments studying thermal stability showed that OPH-SAMMS was significantly more stable than OPH in solution. The results of these experiments are shown in the Tables below.

|  | OPH Soluble Storage Time, days | | | | | | | | |
| --- | --- | --- | --- | --- | --- | --- | --- | --- | --- |
|  | 7 | | | 14 | | | 30 | | |
| Temperature, ° C. | 4 | room | 37 | 4 | room | 37 | 4 | room | 37 |
| Activity % | 95 | 85 | 80 | 92 | 80 | 65 | 90 | 75 | 50 |

|  | OPH-SAMMS Storage Time, days | | | | | | | | |
| --- | --- | --- | --- | --- | --- | --- | --- | --- | --- |
|  | 7 | | | 14 | | | 30 | | |
| Temperature, ° C. | 4 | room | 37 | 4 | room | 37 | 4 | room | 37 |
| Activity % | 100 | 100 | 5 | 105 | 107 | 85 | 102 | 103 | 80 |

Example 13

Effect Of Lyophilization

OPH-SAMMS and soluble OPH were subjected to lyophilization conditions (1M MES, pH 5.0) and it was found that OPH-SAMMS retained 50% of its activity after 1 and 24 hours, while the soluble OPH retained only 15% of its activity after 1 and 24 hours.

This invention may include various modifications and alterations without departing from the spirit and scope of the invention. Thus, it should be understood that the invention is not to be limited to the specific descriptions and examples, but it is to be controlled by the limitations set forth in the following claims and equivalents of the elements set forth in the claims.

We claim:

1. An enzyme system comprising:
   a porous matrix material having a pore volume wherein at least 90% of the pore volume is composed of pores having sizes in the range of 50 to 400 Å, and
   further comprising an enzyme bonded to the matrix material, wherein said enzyme occupies between 5 and 40% of the average pore volume, wherein the enzyme system comprises at least 8 mg of said enzyme per gram of matrix material and wherein said enzyme in the enzyme system exhibits an activity that is at least 65% of the enzyme's activity outside the matrix when activity of the enzyme inside the matrix and outside the matrix is measured under otherwise identical conditions including the same buffer conditions and same temperature, and expressed in unit activity per mass of enzyme.

2. The system of claim 1 wherein the enzyme system comprises 8 to 125 mg of said enzyme per gram of matrix material and wherein at least 90% of the pore volume is composed of pores having sizes in the range of 100 to 200 Å.

3. The system of claim 1 wherein said enzyme is organohydrolase (OPH).

4. The system of claim 1 wherein the enzyme has a volume in the range of $0.5 \times 10^5$ Å$^3$ to $3 \times 10^5$ Å$^3$.

5. The system of claim 4 wherein the volume of the enzyme is in the range of 10 to 25% of the average pore volume.

6. The system of claim 4 wherein the surface area of the porous matrix material is at least 700 m$^2$/g.

7. The system of claim 3 wherein said system comprises between 5 and 25 mg OPH per cubic centimeter.

8. The system of claim 3 wherein the OPH has a $V_{max}$ of 0.15 to 0.66 AU/s.

9. The system of claim 3 wherein the system retains about 10% of its activity after 24 hours in 1M Tris at 12.0 pH.

10. The system of claim 1 wherein the matrix is a self-assembled monolayer on mesoporous silica (SAMMS).

11. The enzyme system of claim 1 wherein at least 90% of the pore volume is composed of pores having sizes in the range of 100 to 120 Å.

12. The enzyme system of claim 1 wherein the enzyme is bonded to the porous matrix through 2 to 10 connecting moieties.

13. The enzyme system of claim 1 wherein the enzyme is bonded to the porous matrix through a moiety having a chain length of 2 to 20 atoms.

14. The enzyme system of claim 12 wherein the enzyme is bonded to the porous matrix through a moiety having a chain length of 2 to 20 atoms.

15. The enzyme system of claim 1 wherein the enzyme is bonded to the porous matrix through a moiety having a chain length of 4 to 10 atoms.

16. Filtration equipment comprising the system of claim 1.

17. A chemical process catalyzed by the system of claim 1, comprising:
    contacting a reactant with the system of claim 1 wherein the enzyme in the system of claim 1 catalyzes the conversion of the reactant to a product; and
    forming the product.

18. The process of claim 17 selected from the group consisting of hydrolysis, oxidation, hydrogenation, and proteolysis.

19. An enzyme system comprising:
    a porous matrix material having a pore volume wherein at least 90% of the pore volume is composed of pores having sizes in the range of 50 to 400 Å and
    further comprising an enzyme bonded to the matrix material, wherein said enzyme occupies between 5 and 40% of the average pore volume, wherein said enzyme is OPH having an activity of 60 to 95% of the enzyme's activity outside the matrix when activity of the enzyme inside the matrix and outside the matrix is measured under otherwise identical conditions including the same buffer conditions and same temperature, and expressed in unit activity per mass of enzyme.

20. An enzyme system comprising:
    a porous matrix material and an enzyme;
    wherein the porous matrix material has a pore volume wherein at least 90% of the pore volume is composed of pores having sizes in the range of 50 to 400 Å; and comprising at least 8 mg of enzyme per gram of matrix material and wherein said enzyme in the enzyme system exhibits an activity that is at least 65% of the enzyme's activity outside the matrix when activity of the enzyme inside the matrix and outside the matrix is measured under otherwise identical conditions including the same buffer conditions and same temperature, and expressed in unit activity per mass of enzyme.

21. The enzyme of claim 20 wherein said enzyme occupies between 5 and 40% of the average pore volume.

22. The enzyme system of claim 20 wherein said enzyme is organohydrolase (OPH).

23. The enzyme system of claim 20 wherein the matrix is a mesoporous oxide material.

24. The enzyme system of claim 20 wherein at least 90% of the pore volume is composed of pores having sizes in the range of 100 to 120 Å.

25. A chemical process catalyzed by the system of claim 16, comprising:
    contacting a reactant with the system of claim 20 wherein the enzyme in the system of claim 20 catalyzes the conversion of the reactant to a product; and
    forming the product.

* * * * *

SEQUENCE LISTING

<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: Primers were designed to yield a PCR
      (polymerase chain reaction) product from the ATCC clone that
      would contain the full-length OPH open reading frame as well as
      appropriate restriction sites at the 5' and 3' ends for ligation
      into the pET expression vectors.

<400> SEQUENCE: 1
taaattatct ctggcggtgt tgacat                                          26

<210> SEQ ID NO 2
<211> LENGTH: 20
<212> TYPE: DNA
<213> ORGANISM: Artificial Sequence
<220> FEATURE:
<223> OTHER INFORMATION: Primers were designed to yield a PCR
      (polymerase chain reaction) product from the ATCC clone that
      would contain the full-length OPH open reading frame as well as
      appropriate restriction sites at the 5' and 3' ends for ligation
      into the pET expression vectors.

<400> SEQUENCE: 2
gaaggatcca gatggcgtca                                                 20

<210> SEQ ID NO 3
<211> LENGTH: 1029
<212> TYPE: DNA
<213> ORGANISM: Unknown
<220> FEATURE:
<223> OTHER INFORMATION: The organism is unknow per ATCC (#67778)

<400> SEQUENCE: 3
cgtcatgacg cccgcaaggt cggtgacaag aaccgcgccg ggttagtcac agtgatgcct     60
gccagcgttt gctgtgggac gcccttctct cgtaggaatg ggatcactct cagtggaatg    120
aaggccatcc cgtcggggtt cacgcgatcc atcacgtcca tgatgttggt gacatagctc    180
gaaaacccga acagccagtc attcgaaacg aggatttgtt tcatgtagcc ttggtcgatg    240
agcgccttga tcaagagagc ccgtgtttgc cacgaacgga tgcccaggag ggctgatgca    300
ctcgcattat cttctagacc aatcgcactg tgcgggatgt ggtctagacc gatgaggtat    360
ccgcgcgcag cgagggcggt gagatagctc aaatcgtcag tatcatcgct gtgaccaata    420
caaacccgtg aggggctcaa gccttcggac tcaaaaatgg cggcctgctg ctcaccatcg    480
cgctgacttg ctgccgtgtg agtggttacc ggaacaccgg tggccaagct ggcccgggcg    540
gccgccttta acactaactc ctgaaagggg gtcgccttgc ctgtggtcgc gaccttgata    600
atgcccgccc taattccggt gtcttcgatg ccatattgaa tctcacgcag gaagaactgt    660
gtgagttcct ctacactcct caatcgcatc gaaagtggcg ggtcgaacca caagccggtc    720
gccgccacga tatgaacgtc ggcagcccgc gaaacctcgg ccaataaact gacgtcgcga    780
ccgatatcga aagtcgacac atcgacaatc gttcgcacgc cagccgctct ggcgcggcgc    840
aatcctctca cagcctttc cgctagagct ttgcggctac cgaagaactc tggccaagca    900
cgcaagaatc ctgccgagct gccgcagatg tgctcgtgag tcagtgtgaa acccgcttca    960
gagattgtga taggaccacg aacggtgttg atacggtcac cggtaccgat agacatatgt   1020
atatctcct                                                           1029

```
<210> SEQ ID NO 4
<211> LENGTH: 337
<212> TYPE: PRT
<213> ORGANISM: Unknown
<220> FEATURE:
<223> OTHER INFORMATION: The sequence is the resulting protein encoded
      by the OPH gene which has no identifying organism of origin per
      ATCC (#67778).

<400> SEQUENCE: 4

Met Ser Ile Gly Thr Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Ala Glu Lys Ala Val Arg Gly Leu Arg Arg Ala Arg Ala
50                  55                  60

Ala Gly Val Arg Thr Ile Val Asp Val Ser Thr Phe Asp Ile Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Phe Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
    130                 135                 140

Thr Gly Lys Ala Thr Pro Phe Gln Glu Leu Val Leu Lys Ala Ala Ala
145                 150                 155                 160

Arg Ala Ser Leu Ala Thr Gly Val Pro Val Thr Thr His Thr Ala Ala
                165                 170                 175

Ser Gln Arg Asp Gly Glu Gln Gln Ala Ala Ile Phe Glu Ser Glu Gly
            180                 185                 190

Leu Ser Pro Ser Arg Val Cys Ile Gly His Ser Asp Asp Thr Asp Asp
        195                 200                 205

Leu Ser Tyr Leu Thr Ala Leu Ala Ala Arg Gly Tyr Leu Ile Gly Leu
    210                 215                 220

Asp His Ile Pro His Ser Ala Ile Gly Leu Glu Asp Asn Ala Ser Ala
225                 230                 235                 240

Ser Ala Leu Leu Gly Ile Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Phe Ser Ser Tyr Val Thr Asn Ile Met Asp Val
        275                 280                 285

Met Asp Arg Val Asn Pro Asp Gly Met Ala Phe Ile Pro Leu Arg Val
    290                 295                 300

Ile Pro Phe Leu Arg Glu Lys Gly Val Pro Gln Gln Thr Leu Ala Gly
305                 310                 315                 320

Ile Thr Val Thr Asn Pro Ala Arg Phe Leu Ser Pro Thr Leu Arg Ala
                325                 330                 335

Ser
```